United States Patent [19]

van der Knaap

[11] Plant 5,009

[45] Mar. 22, 1983

[54] CHRYSANTHEMUM NAMED SNOW WESTLAND

[75] Inventor: Jacques C. M. van der Knaap, De Lier, Netherlands

[73] Assignee: Pan-American Plant Company, Parrish, Fla.

[21] Appl. No.: 193,032

[22] Filed: Oct. 2, 1980

[51] Int. Cl.[3] ..... A01H 5/00

[52] U.S. Cl. ..... Plt./76

[58] Field of Search ..... Plt./74–83

*Primary Examiner*—James R. Feyrer

*Attorney, Agent, or Firm*—Chas. W. Rummler

[57] ABSTRACT

A new and unique spray-type chrysanthemum intended for greenhouse culture to produce pot plants and cut flowers, this plant being distinguished by its generally white flowers which have spoon-tipped ray florets, its medium sized blooms which vary in size from 6 to 10 cm. in diameter, and a lasting quality of about four weeks both on the plant and as a cut flower. The title of this application is the European denomination for this variety. In the United States, this variety is marketed as "Westland Snow".

4 Drawing Figures

BACKGROUND OF THE NEW PLANT

This new variety originated as a spontaneous sport of "Westland" (U.S. Plant Pat. No. 4,589) and was discovered by me in 1976 at De Lier, Holland, in the course of my breeding work being carried on with the object of producing new chrysanthemum varieties. The unusual character of this plant prompted me to reproduce the plant for test purposes by means of cuttings at De Lier, Holland. Subsequent propagation through successive generations has shown that this cultivar holds its distinguishing characteristics from generation to generation and this novelty appears to be firmly fixed. This variety is now being commercially propagated at West Chicago, Ill., and at Cortez, Fla., as well as De Lier, Holland.

DESCRIPTION OF THE DRAWINGS

This chrysanthemum cultivar is illustrated by the accompanying drawings, of which sheet 1 is a full color photographic view of a potted plant in full bloom, sheet 2 is a print showing a full face view of a flower of this variety showing its petal form and arrangement, and sheets 3 and 4 are prints of machine copies of the front and back sides, respectively, of typical leaves of this new plant.

DESCRIPTION OF THE NEW PLANT

The following is a detailed description of my new variety of chrysanthemum based upon observations made at West Chicago, Ill., U.S.A., in the Fall of 1979, with color designations according to the R.H.S. Colour Chart published by The Royal Horticultural Society of London, England.

THE PLANT

Origin: Sport.
Parentage: Westland (U.S. Plant Pat. No. 4,589).
Classification:
- *Botanic.*—Chrysanthemum morifolium.
- *Commercial.*—Spray chrysanthemum for cut flowers.

Form: Herbaceous bush.
Height: Varies, from about 100 to 125 cm.

Growth: Terminal; strong, vigorous and upright.
Branching: None. Single stem with cyme-type florescence.
Foliage:
- *Quantity.*—Abundant.
- *Leaf size.*—About 25 to 100 mm. long and about 20 to 80 mm. wide.
- *Shape.*—Ovate with cleft margin.
- *Surface texture.*—Leathery.
- *Venation.*—Pinnate.
- *Color.*—Upper side — 147A. Under side — 147B.

Petioles:
- *Length.*—About 10 to 35 mm.

THE BUD

Form: Globular.
Size:
- *Diameter.*—About 8 to 10 mm.
- *Length.*—About 6 to 8 mm.

Opening Rate: Normal.
Phyllaries:
- *Number.*—Approximately 15.
- *Shape.*—Lanceolate.
- *Color.*—138A.

Color of florets:
- *When phyllaries first divide.*—155B.
- *When petals begin to unfurl.*—155B.

Peduncle of flower stems:
- *Character.*—Rigid and erect.
- *Length.*—Varies from about 8 to 19 cm.
- *Surface texture.*—Canescent.
- *Color.*—138B.

THE FLOWER

Blooming habit: Normally intermittent.
Recommended flowering: Year around with photoperiod control.
Response: About 9 weeks.
Blooms:
- *Flower type.*—Composite.
- *Size.*—Medium. Diameter — About 60 to 100 mm. Depth — About 10 to 15 mm.

Borne: Cymosely on a strong, upright main stem.
Shape: Cup-shaped when bloom first opens, becoming flat as bloom matures.

Petalage: Many ray florets and few disc florets.

*Arrangement.*—Imbricated.

*Floret form.*—Spoon tip with entire margin and rounded incised apex.

Texture: Soft.

Appearance: Satiny.

Color:

*Outer florets.*—Upper side — 155B. Reverse side — 155B.

*Inner florets.*—Upper side — 2-B. Reverse side — 2-B.

Persistence: Flowers hang on and dry.

Fragrance: Typical chrysanthemum.

Lasting quality:

*On plant.*—4 weeks.

*As cut flower.*—4 weeks.

REPRODUCTIVE ORGANS

Stamens: Few in number and with syngenesious arrangement.

Pistils:

*Number.*—One for each ray floret.

*Styles.*—About 4 to 6 mm. long. Color: Greenish-Yellow.

*Stigmas.*—Color: Greenish Yellow.

Ovaries: Inferior bicarpellate.

The flower of this variety is particularly distinguished by its white color and spoon-tipped ray floret. Otherwise the plant itself is very much the same as its parent, "Westland", with respect to growth and blooming habits and its usefulness.

I claim:

1. A new and distinct chrysanthemum cultivar, substantially as herein shown and described, characterized by its white spoon-tipped ray florets radiating from inner florets of a very light yellow color.

* * * * *

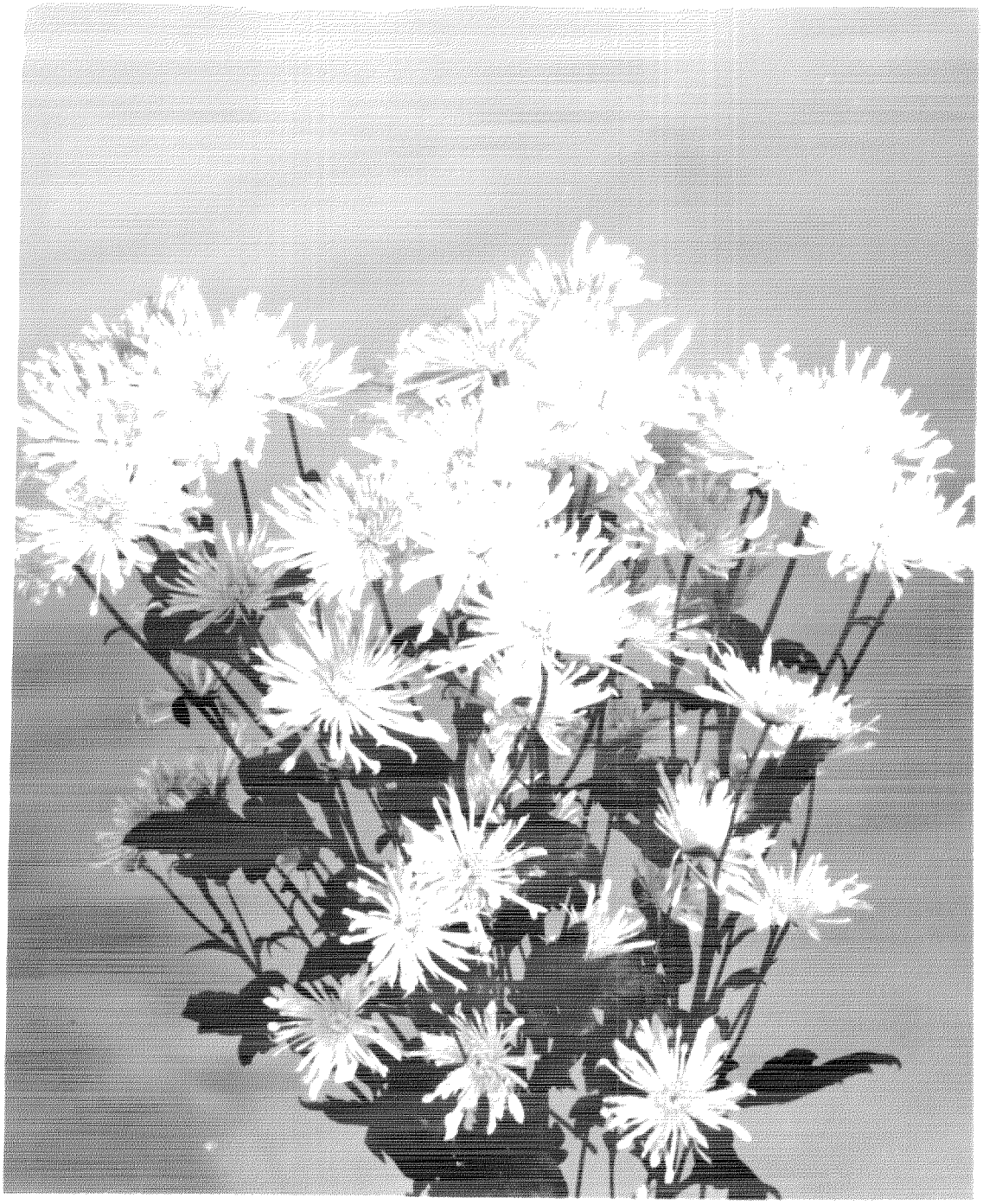

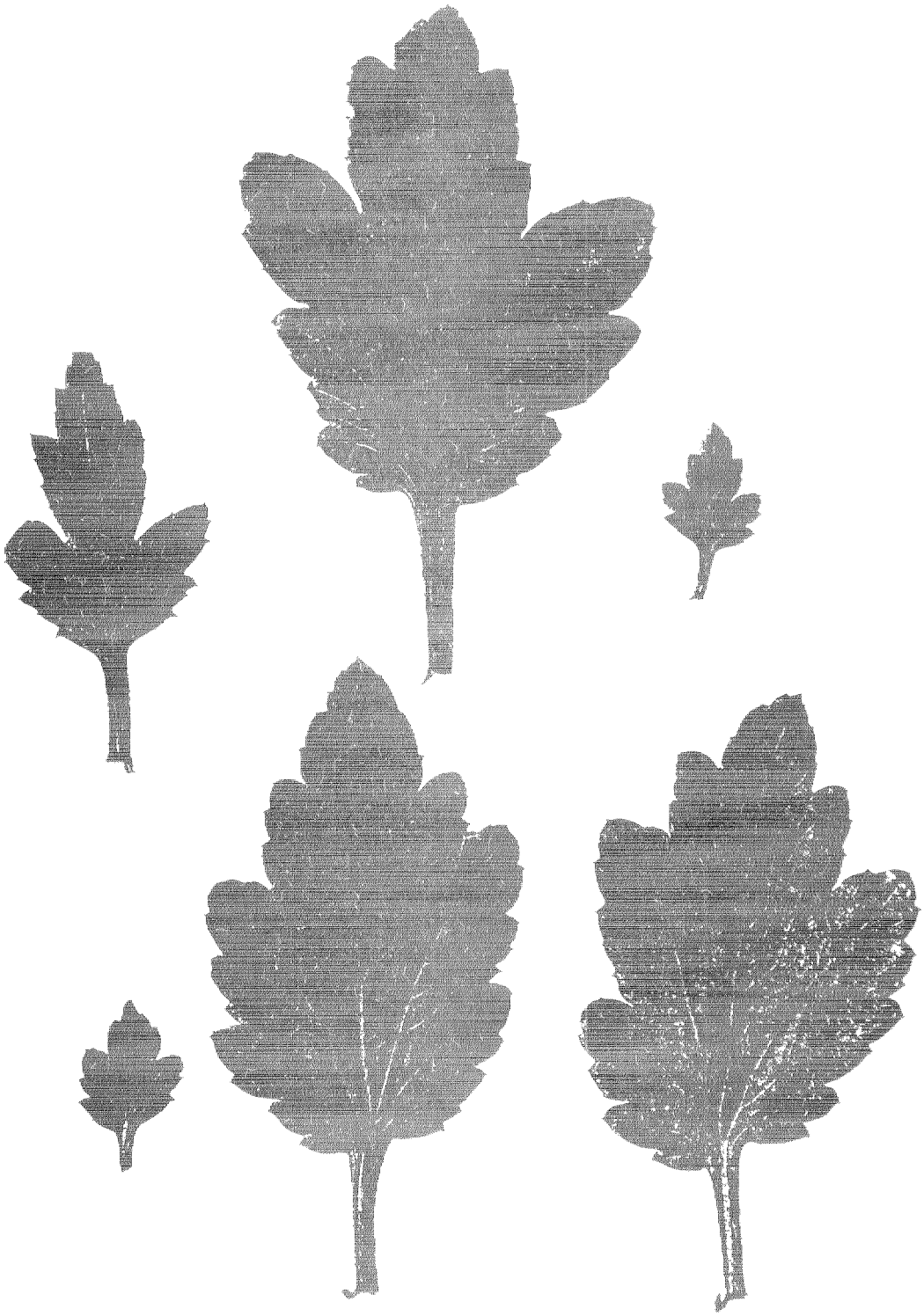

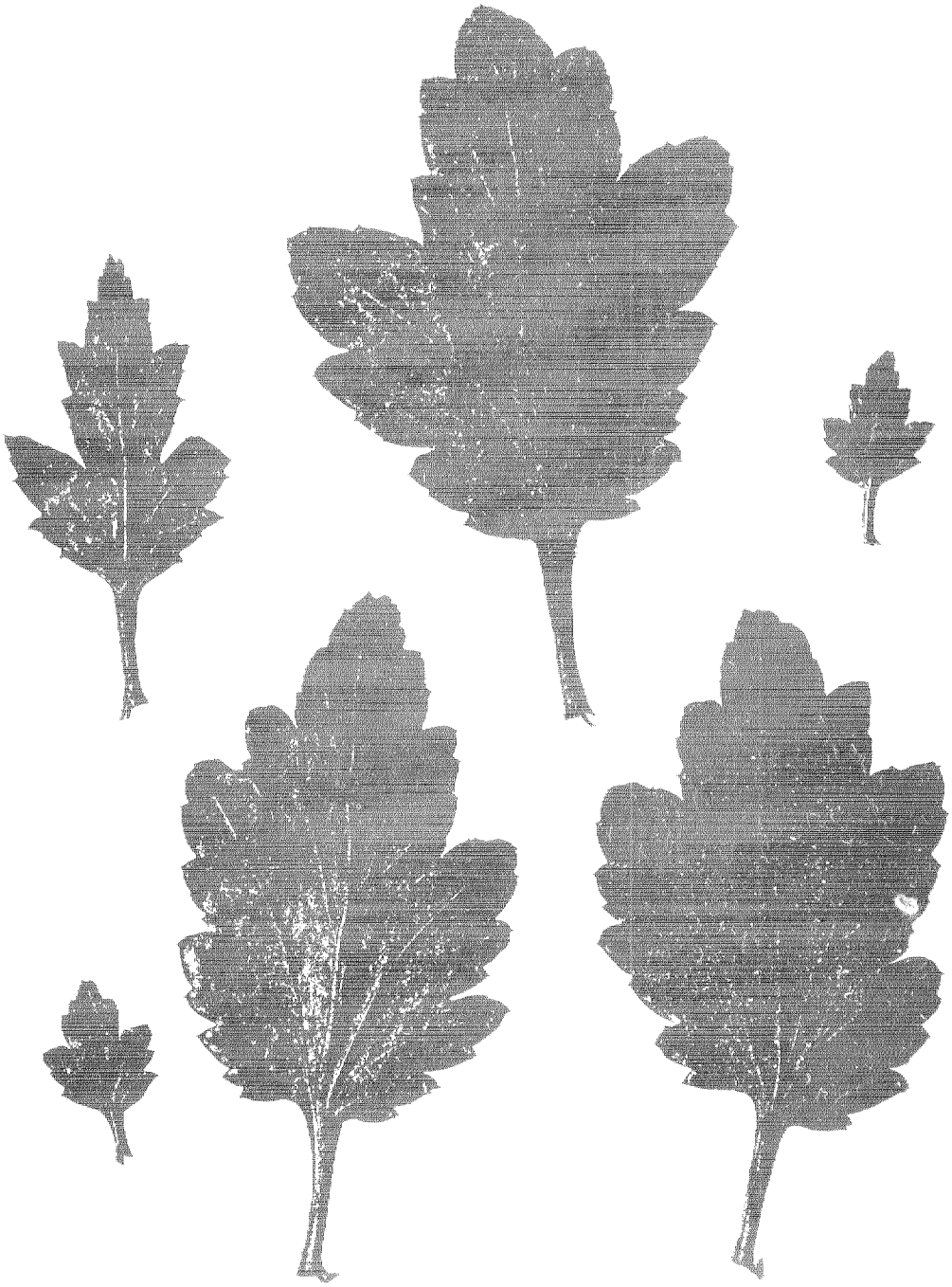

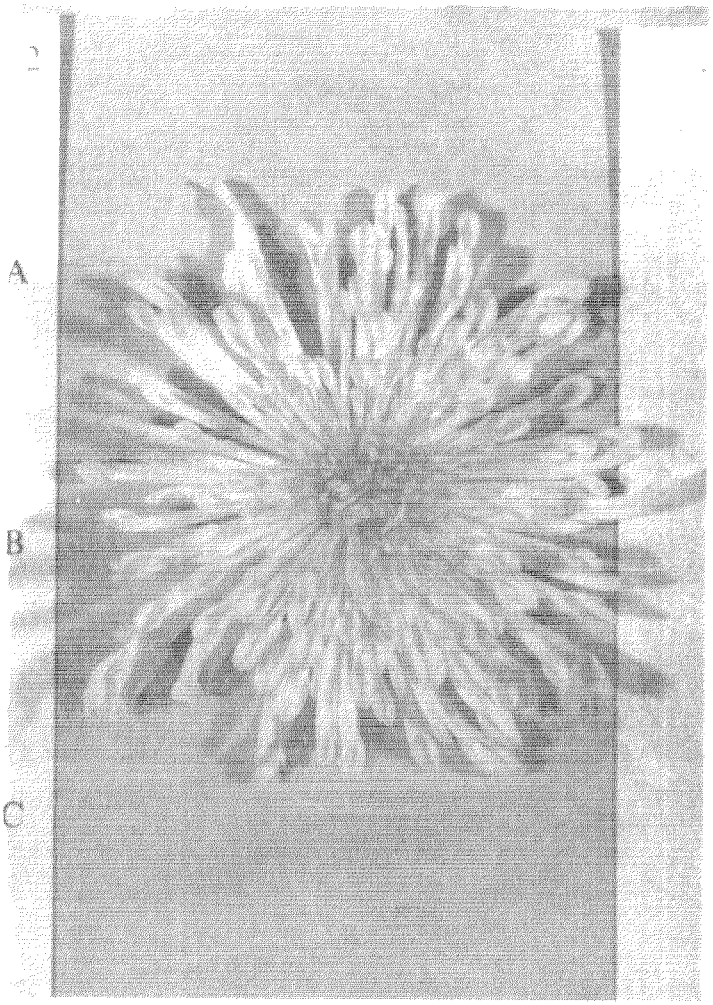
A
B
C